US012428654B1

(12) United States Patent
Thompson

(10) Patent No.: US 12,428,654 B1
(45) Date of Patent: Sep. 30, 2025

(54) COMPOSITION FOR REGULATING PRODUCTION OF PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/929,934

(22) Filed: Oct. 29, 2024

(51) Int. Cl.
*C12N 15/86* (2006.01)
*C07K 14/47* (2006.01)

(52) U.S. Cl.
CPC .......... *C12N 15/86* (2013.01); *C07K 14/4702* (2013.01); *C12N 2750/14143* (2013.01)

(58) Field of Classification Search
CPC .......... C12N 15/86; C12N 2750/14143; C07K 14/4702
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1 | 11/2024 | Thompson | |
| 2024/0026377 A1 | 1/2024 | Thompson | |

FOREIGN PATENT DOCUMENTS

CA 2721333 A1 10/2009

OTHER PUBLICATIONS

O'Brien et al. "Overview of microRNA biogenesis, mechanisms of actions, and circulation." Frontiers in endocrinology 9 (2018): 402.
Gorski et al. "RNA-based recognition and targeting: sowing the seeds of specificity." Nature Reviews Molecular Cell Biology 18.4 (2017): 215-228.
Bottoni et al. "Targeting BTK through microRNA in chronic lymphocytic leukemia." Blood, The Journal of the American Society of Hematology 128.26 (2016): 3101-3112.
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
Kondratov et al. "Direct head-to-head evaluation of recombinant adeno-associated viral vectors manufactured in human versus insect cells." Molecular Therapy 25.12 (2017): 2661-2675.
Nature (2010. Gene Expression. Scitable. Available online at Nature.com) <https://www.nature.com/scitable/topicpage/gene-expression-14121669> (2010).
Brutons Tyrosine Kinase Genbank Sequence (2023).
GenBank EGFR Sequence (2023).
GenBank EGF Sequence (2023).
NCBI search results for Seq ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
NCBI Nucleotide Sequence for PARP, search performed Dec. 26, 2024 (2024).
GenBank FLT3 Sequence (2024).

*Primary Examiner* — Titilayo Moloye
*Assistant Examiner* — Gillian C. Reglas
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in the bioavailability of the target biomolecule within a subject that is administered the one or more compositions. In some embodiments of the present disclosure, the target biomolecule is a protein such as SUMO.

8 Claims, No Drawings

Specification includes a Sequence Listing.

COMPOSITION FOR REGULATING PRODUCTION OF PROTEINS

This application contains a Sequence Listing electronically submitted via Patent Center to the United States Patent and Trademark Office as an XML Document file entitled "A8149888US-SequenceListing.xml" created on 2024 Oct. 23 and having a size of 15,718 bytes. The information contained in the Sequence Listing is incorporated by reference herein.

TECHNICAL FIELD

The present disclosure generally relates to compositions for regulating the production of proteins. In particular, the present disclosure relates to compositions for regulating gene expression and, consequently, the production of proteins that act as neurotrophic factors.

BACKGROUND

Aging in humans can result in decreased levels of neurotrophic factors.

This can result in reduced tissue repair after tissue injury.

As such, it may be desirable to establish therapies, treatments and/or interventions that may induce neurotrophic factors to be endogenously produced in a subject.

SUMMARY

Some embodiments of the present disclosure relate to one or more compositions that upregulate the production of one or more sequences of messenger ribonucleic acid (mRNA). The sequences of mRNA may encode for the translation of a target biomolecule, thereby causing an increase in the bioavailability of the target biomolecule within a subject that is administered the one or more compositions. In some embodiments of the present disclosure, the target biomolecule is a protein such as small ubiquitin-like modifier (SUMO).

In some embodiments of the present disclosure the compositions comprise a plasmid of deoxyribonucleic acid (DNA) that includes one or more insert sequences of nucleic acids that encode for the production of mRNA and a backbone sequence of nucleic acids that facilitates the introduction of the one or more insert sequences into one or more of a subject's cells where it is thereby expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The nucleotide sequence of SEQ ID NO. 1 and SEQ ID NO. 2 encodes e for one or more nucleotide sequences that encode for an mRNA sequence that encodes for the protein SUMO.

Some embodiments of the present disclosure relate to a method of making a composition/target cell complex. The method comprises a step of administering an RP comprising SEQ ID NO. 1 and SEQ ID NO. 2 to a target cell for forming the composition/target cell complex, wherein the composition/target cell complex causes the target cell to increase the production of one or more sequences of mRNA that consequently increases the production of a target biomolecule.

Embodiments of the present disclosure relate to at least one approach for inducing the endogenous production of one or more sequences of mRNA that encodes for a target biomolecule, for example SUMO. A first approach utilizes gene vectors containing nucleotide sequences for increasing the endogenous production of one or more sequences of mRNA, which are complete or partial sequences of SUMO and/or combinations thereof, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present disclosure. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, the composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for the production of at least one sequence of mRNA that increases the production of target biomolecules, such as a protein.

In some embodiments of the present disclosure, the target biomolecule is SUMO.

Some embodiments of the present disclosure relate to a composition that can be administered to a subject with a condition that results, directly or indirectly, from the dysregulated production of a biomolecule. When a therapeutically effective amount of the composition is administered to the subject, the production and/or functionality of one or more of the subject's biomolecules may change as a result.

In some embodiments of the present disclosure, the production and/or functionality of one or more of the subject's intermediary molecules may change in response to the subject receiving a therapeutic amount of the composition, thereby changing production of one or more DNA sequences, one or more RNA sequences, and/or one or more proteins that regulate the levels and/or functionality of the one or more intermediary molecules. The one or more intermediary molecules may regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one biomolecule, such as SUMO.

In some embodiments of the present disclosure, the delivery vehicle for the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle for the RP used for gene therapy may be a protein coat.

In some embodiments of the present disclosure, the delivery vehicle for the RP used for gene therapy may be a lipid vesicle.

The embodiments of the present disclosure also relate to the administration of a therapeutically effective amount of the composition. In some embodiments of the present disclosure, the therapeutically effective amount of the composition that is administered to a patient is between about 10 and about $1\times10^{16}$ TCID$_{50}$/kg (50% tissue culture infective dose per kilogram of the patient's body mass). In some embodiments of the present disclosure, the therapeutically effective amount of the composition that is administered to the patient is about $1\times10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that, when operable inside a target cell, will cause the target cell to produce an mRNA sequence that upregulates the production of a biomolecule, with an example being SUMO. The RP is comprised of AAV2 inverted terminal repeats (ITRs), a composite CASI promoter, and a human growth hormone (HGH) signal peptide followed by a mRNA expression cassette encoding for SUMO, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
TCTAGAGATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG

CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT
```

-continued

```
GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

ATGAATTTATCAGCTAGAACGGTTGAATATCATATTGATGGTGATTTGACTGTCTCC

GGCCTTTCTCACCCGTTTGAATCTTTACCTACACATTACTCAGGCATTGCATTTAAAA

TATATGAGGGTTCTAAAAATTTTTATCCTTGCGTTGAAATAAAGGCTTCTCCCGCAA

AAGTATTACAGGGTCATAATGTTTTTGGTACAACCGATTTAGCTTTATGCTCTGAGG

CTTTATTGCTTAATTTTGCTAATTCTTTGCCTTGCCTGTATGATTTATTGGATGTTGGA

ATTCCTGATGCGGTATTTTCTCCTTACGCATCTGTGCGGTATTTCACACCGCATATGG

TGCACTCTCAGTACAATCTGCTCTGATGCCGCATAGTTAAGCCAGCCCCGACACCCG

CCAACACCCGCTGACGCGCCCTGACGGGCTTGTCTGCTCCCGGCATCCGCTTACAGA

CAAGCTGTGACCGTCTCCGGGAGCTGCATGTGTCAGAGGTTTTCACCGTCATCACCG

AAACGCGCGAGACGAAAGGGCCTCGTGATACGCCTATTTTTATAGGTTAATGTCATG

ATAATAATGGTTTCTTAGACGTCAGGTGGCACTTTTCGGGGAAATGTGCGCGGAACC

CCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCC

GTGTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCACGAGTGGGTTACAT

CGAACTGGATCTCAACAGCGGTAAGATCCTTGAGAGTTTTCGCCCCGAAGAACGTTT

TCCAATGATGAGCACTTTTAAAGTTCTGCTATGTGGCGCGGTATTATCCCGTATTGAC

GCCGGGCAAGAGCAACTCGGTCGCCGCATACACTATTCTCAGAATGACTTGGTTGAG

TACTCACCAGTCACAGAAAAGCATCTTACGGATGGCATGACAGTAAGAGAATTATG

CAGTGCTGCCATAACCATGAGTGATAACACTGCGGCCAACTTACTTCTGACAACGAT

CGGAGGACCGAAGGAGCTAACCGCTTTTTTGCACAACATGGGGGATCATGTAACTC

GCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACT

ACTTACTCTAGCTTCCCGGCAACAATTAATAGACTGGATGGAGGCGGATAAAGTTGC

AGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGC

CCTCCCGTATCGTAGTTATCTACACGACGGGGAGTCAGGCAACTATGGATGAACGA

AATAGACAGATCGCTGAGATAGGTGCCTCACTGATTAAGCATTGGTAACTGTCAGAC

CAAGTTTACTCATATATACTTTAGATTGATTTAAAACTTCATTTTTAATTTAAAAGGA

TCTAGGTGAAGATCCTTTTTGATAATCTCATGACCAAAATCCCTTAACGTGAGTTTTC

GTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAG

AGCGCAGATACCAAATACTGTCCTTCTAGTGTAGCCGTAGTTAGGCCACCACTTCAA

GAACTCTGTAGCACCGCCTACATACCTCGCTCTGCTAATCCTGTTACCAGTGGCTGC
```

-continued

```
TGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGC

GAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAG

GAGAGCGCACGAGGGAGCTTCCAGGGGGAAACGCCTGGTATCTTTATAGTCCTGTC

GGGTTTCGCCACCTCTGACTTGAGCGTCGATTTTTGTGATGCTCGTCAGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTTAATTATTTTG

TGCAGCGATGGGGGCGGGGGGGGGGGGGCGCGCGCCAGGCGGGGCGGGGGGG

GCGAGGGGCGGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGCGGTGAACGCCGATGATGCCTCTACTAACCATGTTCATGTTTTCTT

TTTTTTTCTACAGGTCCTGGGTGACGAACAGGGTACC
```

3'

SEQ ID NO. 2 (mRNA expression cassette No. 2 - SUMO):
5'

```
GCCACCATGGCGACGGGTTCAAGAACTTCCCTACTTCTTGCATTTGGCCTGCTTTGTT

TGCCGTGGTTACAGGAGGGCTCGGCAATGAGCGATCAGGAAGCGAAACCGAGCACC

GAAGATCTGGGCGATAAAAAAGAAGGCGAATATATTAAACTGAAAGTGATTGGCCA

GGATAGCAGCGAAATTCATTTTAAAGTGAAAATGACCACCCATCTGAAAAAACTGA

AAGAAAGCTATTGCCAGCGCCAGGGCGTGCCGATGAACAGCCTGCGCTTTCTGTTTG
```

-continued

AAGGCCAGCGCATTGCGGATAACCATACCCCGAAAGAACTGGGCATGGAAGAAGA

AGATGTGATTGAAGTGTATCAGGAACAGACCGGCGGCCATAGCACCGTGTCTAGAG

AT

3'

SEQ ID NO. 3 = SEQ ID NO. 1 + SEQ ID NO. 2
5'

TCTAGAGATAATCAACCTCTGGATTACAAAATTTGTGAAAGATTGACTGGTATTCTT

AACTATGTTGCTCCTTTTACGCTATGTGGATACGCTGCTTTAATGCCTTTGTATCATG

CTATTGCTTCCCGTATGGCTTTCATTTTCTCCTCCTTGTATAAATCCTGGTTGCTGTCT

CTTTATGAGGAGTTGTGGCCCGTTGTCAGGCAACGTGGCGTGGTGTGCACTGTGTTT

GCTGACGCAACCCCCACTGGTTGGGGCATTGCCACCACCTGTCAGCTCCTTTCCGGG

ACTTTCGCTTTCCCCCTCCCTATTGCCACGGCGGAACTCATCGCCGCCTGCCTTGCCC

GCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGAC

GTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCT

CCCTTTGGGCCGCCTCCCCGCCTAAGCTTATCGATACCGTCGAGATCTAACTTGTTTA

TTGCAGCTTATAATGGTTACAAATAAAGCAATAGCATCACAAATTTCACAAATAAAG

CATTTTTTTCACTGCATTCTAGTTGTGGTTTGTCCAAACTCATCAATGTATCTTATCAT

GTCTGGATCTCGACCTCGACTAGAGCATGGCTACGTAGATAAGTAGCATGGCGGGTT

AATCATTAACTACAAGGAACCCCTAGTGATGGAGTTGGCCACTCCCTCTCTGCGCGC

TCGCTCGCTCACTGAGGCCGGGCGACCAAAGGTCGCCCGACGCCCGGGCTTTGCCC

GGGCGGCCTCAGTGAGCGAGCGAGCGCGCCAGCTGGCGTAATAGCGAAGAGGCCC

GCACCGATCGCCCTTCCCAACAGTTGCGCAGCCTGAATGGCGAATGGAATTCCAGA

CGATTGAGCGTCAAAATGTAGGTATTTCCATGAGCGTTTTTCCTGTTGCAATGGCTG

GCGGTAATATTGTTCTGGATATTACCAGCAAGGCCGATAGTTTGAGTTCTTCTACTC

AGGCAAGTGATGTTATTACTAATCAAAGAAGTATTGCGACAACGGTTAATTTGCGTG

ATGGACAGACTCTTTTACTCGGTGGCCTCACTGATTATAAAAACACTTCTCAGGATT

CTGGCGTACCGTTCCTGTCTAAAATCCCTTTAATCGGCCTCCTGTTTAGCTCCCGCTC

TGATTCTAACGAGGAAAGCACGTTATACGTGCTCGTCAAAGCAACCATAGTACGCG

CCCTGTAGCGGCGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCC

ACGTTCGCCGGCTTTCCCCGTCAAGCTCTAAATCGGGGGCTCCCTTTAGGGTTCCGA

TTTAGTGCTTTACGGCACCTCGACCCCAAAAAACTTGATTAGGGTGATGGTTCACGT

AGTGGGCCATCGCCCTGATAGACGGTTTTTCGCCCTTTGACGTTGGAGTCCACGTTCT

TTAATAGTGGACTCTTGTTCCAAACTGGAACAACACTCAACCCTATCTCGGTCTATTC

TTTTGATTTATAAGGGATTTTGCCGATTTCGGCCTATTGGTTAAAAAATGAGCTGATT

TAACAAAAATTTAACGCGAATTTTAACAAAATATTAACGTTTACAATTTAAATATTT

GCTTATACAATCTTCCTGTTTTTGGGGCTTTTCTGATTATCAACCGGGGTACATATGA

TTGACATGCTAGTTTTACGATTACCGTTCATCGATTCTCTTGTTTGCTCCAGACTCTC

AGGCAATGACCTGATAGCCTTTGTAGAGACCTCTCAAAAATAGCTACCCTCTCCGGC

-continued

```
ATGAATTTATCAGCTAGAACGGTTGAATATCATATTGATGGTGATTTGACTGTCTCC
GGCCTTTCTCACCCGTTTGAATCTTTACCTACACATTACTCAGGCATTGCATTTAAAA
TATATGAGGGTTCTAAAAATTTTTATCCTTGCGTTGAAATAAAGGCTTCTCCCGCAA
AAGTATTACAGGGTCATAATGTTTTTGGTACAACCGATTTAGCTTTATGCTCTGAGG
CTTTATTGCTTAATTTTGCTAATTCTTTGCCTTGCCTGTATGATTTATTGGATGTTGGA
ATTCCTGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACC
CCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACAT
CGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTC
GCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGG
AGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAA
GAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGC
GAACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTC
```

-continued
```
GGGTTTCGCCACCTCTGACTTGAGCGTCGATTTTTGTGATGCTCGTCAGGGGGCGG

AGCCTATGGAAAAACGCCAGCAACGCGGCCTTTTTACGGTTCCTGGCCTTTTGCTGG

CCTTTTGCTCACATGTTCTTTCCTGCGTTATCCCCTGATTCTGTGGATAACCGTATTAC

CGCCTTTGAGTGAGCTGATACCGCTCGCCGCAGCCGAACGACCGAGCGCAGCGAGT

CAGTGAGCGAGGAAGCGGAAGAGCGCCCAATACGCAAACCGCCTCTCCCCGCGCGT

TGGCCGATTCATTAATGCAGCAGCTGCGCGCTCGCTCGCTCACTGAGGCCGCCCGGG

CAAAGCCCGGGCGTCGGGCGACCTTTGGTCGCCCGGCCTCAGTGAGCGAGCGAGCG

CGCAGAGAGGGAGTGGCCAACTCCATCACTAGGGGTTCCTTGTAGTTAATGATTAAC

CCGCCATGCTACTTATCTACGTAGCCATGCTCTAGGACATTGATTATTGACTAGTGG

AGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTT

TCCATTGACGTCAATGGGTGGAGTATTTACGGTAAACTGCCCACTTGGCAGTACATC

AAGTGTATCATATGCCAAGTACGCCCCCTATTGACGTCAATGACGGTAAATGGCCCG

CCTGGCATTATGCCCAGTACATGACCTTATGGGACTTTCCTACTTGGCAGTACATCTA

CGTATTAGTCATCGCTATTACCATGGTCGAGGTGAGCCCCACGTTCTGCTTCACTCTC

CCCATCTCCCCCCCCTCCCCACCCCCAATTTTGTATTTATTTATTTTTTAATTATTTTG

TGCAGCGATGGGGGCGGGGGGGGGGGGGCGCGCGCCAGGCGGGGCGGGGGGG

GCGAGGGGCGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCGAAGCGCGCGGCGGGCGGGAGTCGCTGCGCGCTGCCTTCGCCCCGTGCCCCGC

TCCGCCGCCGCCTCGCGCCGCCCGCCCCGGCTCTGACTGACCGCGTTACTAAAACAG

GTAAGTCCGGCCTCCGCGCCGGGTTTTGGCGCCTCCCGCGGGCGCCCCCCTCCTCAC

GGCGAGCGCTGCCACGTCAGACGAAGGGCGCAGCGAGCGTCCTGATCCTTCCGCCC

GGACGCTCAGGACAGCGGCCCGCTGCTCATAAGACTCGGCCTTAGAACCCCAGTAT

CAGCAGAAGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGCGGAGGG

ATCTCCGTGGGCGGTGAACGCCGATGATGCCTCTACTAACCATGTTCATGTTTTCTT

TTTTTTTCTACAGGTCCTGGGTGACGAACAGGGTACCGCCACCATGGCGACGGGTTC

AAGAACTTCCCTACTTCTTGCATTTGGCCTGCTTTGTTTGCCGTGGTTACAGGAGGGC

TCGGCAATGAGCGATCAGGAAGCGAAACCGAGCACCGAAGATCTGGGCGATAAAA

AAGAAGGCGAATATATTAAACTGAAAGTGATTGGCCAGGATAGCAGCGAAATTCAT

TTTAAAGTGAAAATGACCACCCATCTGAAAAAACTGAAAGAAAGCTATTGCCAGCG

CCAGGGCGTGCCGATGAACAGCCTGCGCTTTCTGTTTGAAGGCCAGCGCATTGCGGA

TAACCATACCCCGAAAGAACTGGGCATGGAAGAAGAAGATGTGATTGAAGTGTATC

AGGAACAGACCGGCGGCCATAGCACCGTGTCTAGAGAT

3'
```

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3 or at the 5' end of SEQ ID NO. 1.

As will be appreciated by those skilled in the art, a perfect match of nucleotides with each of the mRNA expression cassette sequences is not necessary in order to have the desired result of increased bioavailability of the target biomolecule as a result of the target cell producing the mRNA sequence that code for the expression of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes were integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with a sequence of nucleotides that encodes a sequence of messenger ribonucleic acid (mRNA) that encodes for a protein, wherein the sequence of nucleotides is 95% to 100% identical to SEQ ID NO. 2.

2. The composition of claim 1, wherein the RP is configured to be delivered to a target cell.

3. The composition of claim 1, wherein the RP is encased in a protein coat, a lipid vesicle, or any combination thereof.

4. The composition of claim 1, wherein the RP is encased in a viral vector.

5. The compositions of claim 4, wherein the viral vector is one of a double-stranded DNA virus, a single-stranded DNA virus, a single-stranded RNA virus, or a double-stranded RNA virus.

6. The compositions of claim 4, wherein the viral vector is an adeno-associated virus.

7. The composition of claim 1, wherein the protein is small ubiquitin-like modifier (SUMO).

8. A composition that comprises a recombinant plasmid (RP) with a sequence of nucleotides for encoding a sequence of messenger ribonucleic acid (mRNA) that encodes for a protein, wherein the sequence of nucleotides is 95-100% identical to SEQ ID NO. 3, and wherein the protein is small ubiquitin-like modifier (SUMO).

\* \* \* \* \*

SEQUENCE LISTING

```
Sequence total quantity: 3
SEQ ID NO: 1            moltype = DNA   length = 5855
FEATURE                 Location/Qualifiers
source                  1..5855
                        mol_type = other DNA
                        organism = synthetic construct
SEQUENCE: 1
tctagagata atcaacctct ggattacaaa atttgtgaaa gattgactgg tattcttaac    60
tatgttgctc cttttacgct atgtggatac gctgctttaa tgcctttgta tcatgctatt   120
gcttcccgta tggctttcat tttctcctcc ttgtataaat cctggttgct gtctcttat    180
gaggagttgt ggcccgttgt caggcaacgt ggcgtggtgt gcactgtgtt tgctgacgca   240
acccccactg gttggggcat tgccaccacc tgtcagctcc tttccgggac tttcgctttc   300
ccctccctca ttgccacggc ggaactcatc gccgcctgcc ttgcccgctg ctggacaggg   360
gctcggctgt tgggcactga caattccgtg gtgttgtcgg ggaaatcatc gtccttcct    420
tggctgctcg cctgtgttgc cacctggatt ctgcgcggga cgtccttctg ctacgtccct   480
tcggccctca atccagcgga ccttccttcc cgcggcctgc tgccggctct gcggcctctt   540
ccgcgtcttc gccttcgccc tcagacgagt cggatctccc tttgggccgc ctccccgcct   600
aagcttatcg ataccgtcga gatctaactt gtttattgca gcttataatg gttacaaata   660
aagcaatagc atcacaaatt tcacaaataa agcatttttt tcactgcatt ctagttgtgg   720
tttgtccaaa ctcatcaatg tatcttatca tgtctggatc tcgacctcga ctagagcatg   780
gctacgtaga taagtagcat ggcgggttaa tcattaacta caaggaaccc ctagtgatgg   840
agttggccac tccctctctg cgcgctcgct cgctcactga ggccgggcga ccaaaggtcg   900
cccgacgccc gggctttgcc cgggcggcct cagtgagcga gcgagcgcgc cagctggcgt   960
aatagcgaag aggcccgcac cgatcgccct tcccaacagt tgcgcagcct gaatggcgaa  1020
tggaattcca gacgattgag cgtcaaaatg taggtatttc catgagcgtt tttcctgttg  1080
caatggctgg cggtaatatt gttctggata ttaccagcaa ggccgatagt ttgagttctt  1140
ctactcaggc aagtgatgtt attactaatc aaagaagtat tgcgacaacg gttaatttgc  1200
gtgatggaca gactctttta ctcggtggcc tcactgatta taaaaacact tctcaggatt  1260
ctggcgtacc gttcctgtct aaaatccctt taatcggcct cctgtttagc tcccgctctg  1320
attctaacga ggaaagcacg ttatacgtgc tcgtcaaagc aaccatagta cgcgccctgt  1380
agcggcgcat taagcgcggc gggtgtggtg gttacgcgca gcgtgaccgc tacacttgcc  1440
agcgccctag cgcccgctcc tttcgctttc ttcccttcct ttctcgccac gttcgccggc  1500
tttccccgtc aagctctaaa tcgggggctc cctttagggt tccgatttag tgctttacgg  1560
cacctcgacc ccaaaaaact tgattagggt gatggttcac gtagtgggcc atcgccctga  1620
tagacggttt tcgccctttt gacgttggag tccacgttct ttaatagtgg actcttgttc  1680
caaactggaa caacactcaa ccctatctcg gtctattctt ttgatttata agggattttg  1740
ccgatttcgg cctattggtt aaaaaatgag ctgatttaac aaaaatttaa cgcgaatttt  1800
aacaaaatat taacgtttac aatttaaata tttgcttata caatcttcct gtttttgggg  1860
cttttctgat tatcaaccgg ggtacatatg attgacatgc tagttttacg attaccgttc  1920
atcgattctc ttgtttgctc cagactctca ggcaatgacc tgatagcctt tgtagagacc  1980
tctcaaaaat agctaccctc tccggcatga atttatcagc tagaacggtt gaatatcata  2040
ttgatggtga tttgactgtc tccggccttt ctcacccgtt tgaatcttta cctacacatt  2100
actcaggcat tgcatttaaa atatatgagg gttctaaaaa ttttatcct tgcgttgaaa  2160
taaaggcttc tcccgcaaaa gtattacagg gtcataatgt ttttggtaca accgatttag  2220
ctttatgctc tgaggcttta ttgcttaatt ttgctaattc tttgccttgc ctgtatgatt  2280
tattggatgt tggaattcct gatgcggtat tttctcctta cgcatctgtg cggtatttca  2340
caccgcatat ggtgcactct cagtacaatc tgctctgatg ccgcatagtt aagccagccc  2400
cgacacccgc caacacccgc tgacgcgccc tgacgggctt gtctgctccc ggcatccgct  2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg  2580
ataataatgg tttcttagac gtcaggtggc acttttcggg gaaatgtgcg cggaacccct  2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct ttttgcggc attttgcctt cctgtttttg ctcacccaga aacgctggtg  2820
aaagtaaaag atgctgaaga tcagttgggt gcacgagtgg gttacatcga actggatctc  2880
```

```
aacagcggta agatccttga gagttttcgc cccgaagaac gttttccaat gatgagcact  2940
tttaaagttc tgctatgtgg cgcggtatta tcccgtattg acgccgggca agagcaactc  3000
ggtcgccgca tacactattc tcagaatgac ttggttgagt actcaccagt cacagaaaag  3060
catcttacgg atggcatgac agtaagagaa ttatgcagtg ctgccataac catgagtgat  3120
aacactgcgg ccaacttact tctgacaacg atcggagac cgaaggagct aaccgctttt  3180
ttgcacaaca tggggggatca tgtaactcgc cttgatcgtt gggaaccgga gctgaatgaa  3240
gccataccaa acgacgagcg tgacaccacg atgcctgtag caatggcaac aacgttgcgc  3300
aaactattaa ctggcgaact acttactcta gcttccggc aacaattaat agactggatg  3360
gaggcggata aagttgcagg accacttctg cgctcggccc ttccggctgg ctggtttatt  3420
gctgataaat ctggagccgg tgagcgtggg tctcgcggta tcattgcagc actggggcca  3480
gatggtaagc cctcccgtat cgtagttatc tacacgacgg ggagtcaggc aactatggat  3540
gaacgaaata gacagatcgc tgagataggt gcctcactga ttaagcattg gtaactgtca  3600
gaccaagttt actcatatat actttagatt gatttaaaac ttcattttta atttaaaagg  3660
atctaggtga agatcctttt tgataatctc atgaccaaaa tcccttaacg tgagttttcg  3720
ttccactgag cgtcagaccc cgtagaaaag atcaaaggat cttcttgaga tcctttttt  3780
ctgcgcgtaa tctgctgctt gcaaacaaaa aaaccaccgc taccagcggt ggtttgtttg  3840
ccggatcaag agctaccaac tctttttccg aaggtaactg gcttcagcag agcgcagata  3900
ccaaatactg tccttctagt gtagccgtag ttaggccacc acttcaagaa ctctgtagca  3960
ccgcctacat acctcgctct gctaatcctg ttaccagtgg ctgctgccag tggcgataag  4020
tcgtgtctta ccgggttgga ctcaagacga tagttaccgg ataaggcgca gcggtcgggc  4080
tgaacggggg gttcgtgcac acagcccagc ttggagcgaa cgacctacac cgaactgaga  4140
tacctacagc gtgagctatg agaaagcgcc acgcttccca agggagaaa ggcggacagg  4200
tatccggtaa gcggcagggt cggaacagga gagcgcacga gggagcttcc agggggaaac  4260
gcctggtatc tttatagtcc tgtcgggttt cgccacctct gacttgagcg tcgatttttg  4320
tgatgctcgt cagggggcg gagccatgg aaaaacgcca gcaacgcggc cttttacgg  4380
ttcctggcct tttgctggcc ttttgctcac atgttcttc ctgcgttatc ccctgattct  4440
gtggataacc gtattaccgc ctttgagtga gctgataccg ctcgccgcag ccgaacgacc  4500
gagcgcagcg agtcagtgag cgaggaagcg gaagagcgcc caatacgcaa accgcctctc  4560
cccgcgcgtt ggccgattca ttaatgcagc agctgcgcgc tcgctcgctc actgaggccg  4620
cccggggcaaa gcccgggcgt cgggcgacct ttggtcgccc ggcctcagtg agcgagcgag  4680
cgcgcagaga gggagtggcc aactccatca ctaggggttc cttgtagtta atgattaacc  4740
cgccatgcta cttatctacg tagccatgct ctaggacatt gattattgac tagtggagtt  4800
ccgcgttaca taacttacgg taaatggccc gcctggctga ccgcccaacg accccccgcc  4860
attgacgtca ataatgacgt atgttcccat agtaacgcca ataggggactt tccattgacg  4920
tcaatgggtg gagtatttac ggtaaactgc ccacttggca gtacatcaag tgtatcatat  4980
gccaagtacg ccccctattg acgtcaatga cggtaaatgg cccgcctggc attatgccca  5040
gtacatgacc ttatgggact ttcctacttg gcagtacatc tacgtattag tcatcgctat  5100
taccatggtc gaggtgagcc ccacgttctg cttcactctc cccatctccc ccccctccc  5160
accccaatt ttgtatttat ttattttta attattttgt gcagcgatgg gggcgggggg  5220
ggggggggc gcgcgccagg cgggcgggg cgggcgagg ggcgggggcg ggcgaggcgg  5280
agaggtgcgg cggcagccaa tcagagcggc gcgctccgaa agtttccttt tatggcgagg  5340
cggcggcggc ggcggcccta taaaaagcga agcgcgcggc gggcgggagt cgctgcgcgc  5400
tgccttcgcc cgtgcccg ctccgccgcc gcctcgccgc ccgccccg ctctgactg  5460
accgcgttac taaaacaggt aagtccggcc tccgcgccgg gttttggcgc ctcccgcggg  5520
cgcccctc ctcacggcga gcgctgccac gtcagacgaa gggcgcagcg agcgtcctga  5580
tccttccgcc cggacgctca ggacagcggc ccgctgctca taagactcgg ccttagaacc  5640
ccagtatcag cagaaggaca ttttaggacg ggacttgggt gactctaggg cactggttt  5700
ctttccagag agcggaacag gcgaggaaaa gtagtccctt ctcggcgatt ctgcggaggg  5760
atctccgtgg ggcggtgaac gccgatgatg cctctactaa ccatgttcat gttttcttt  5820
tttttctaca ggtcctggt gacgaacagg gtacc                              5855

SEQ ID NO: 2           moltype = DNA   length = 396
FEATURE                Location/Qualifiers
source                 1..396
                       mol_type = other DNA
                       organism = synthetic construct
SEQUENCE: 2
gccaccatgc cgacgggttc aagaacttcc ctacttcttg catttggcct gctttgtttg   60
ccgtggttac aggagggctc ggcaatgagc gatcaggaag cgaaaccgag caccgaaagt  120
ctgggcgata aaaaagaagg cgaatatatt aaactgaaag tgattggcca ggatagcagc  180
gaaattcatt ttaaagtgaa aatgaccacc catctgaaaa aactgaaaga aagctattgc  240
cagcgccagg gcgtgccgat gaacagcctg cgctttctgt ttgaaggcca gcgcattgcg  300
gataaccata ccccgaaaga actgggcatg gaagaagaag atgtgattga agtgtatcag  360
gaacagaccg gcggccatag caccgtgtct agagat                            396

SEQ ID NO: 3           moltype = DNA   length = 6251
FEATURE                Location/Qualifiers
source                 1..6251
                       mol_type = other DNA
                       organism = synthetic construct
SEQUENCE: 3
tctagagata atcaacctct ggattacaaa atttgtgaaa gattgactgg tattcttaac   60
tatgttgctc ctttttacgct atgtggatac gctgctttaa tgcctttgta tcatgctatt  120
gcttcccgta tggctttcat tttctcctcc ttgtataaat cctggttgct gtctctttat  180
gaggagttgt ggcccgttgt caggcaacgt ggcgtggtgt gcactgtgtt tgctgacgca  240
accccactg gttgggcat tgccaccacc tgtcagctcc tttccgggac tttcgctttc  300
cccctccta ttgccacggc ggaactcatc gccgcctgcc ttgcccgctg ctggacaggg  360
gctcggctgt gggcactga caattccgtg tgttgtcgg gaaatcatc gtcctttcct  420
tggctgctcg cctgtgttgc cacctggatt ctgcgcggga cgtccttctg ctacgtccct  480
```

-continued

```
tcggccctca atccagcgga ccttccttcc cgcggcctgc tgccggctct gcggcctctt  540
ccgcgtcttc gccttcgccc tcagacgagt cggatctccc tttggccgc ctccccgcct   600
aagcttatcg ataccgtcga gatctaactt gtttattgca gcttataatg gttacaaata  660
aagcaatagc atcacaaatt tcacaaataa agcattttt tcactgcatt ctagttgtgg   720
tttgtccaaa ctcatcaatg tatcttatca tgtctggatc tcgacctcga tagagcatg   780
gctacgtaga taagtagcat ggcggggttaa tcattaacta caaggaaccc ctagtgatgg  840
agttggccac tccctctctg cgcgctcgct cgctcactga ggccgggcga ccaaaggtcg   900
cccgacgccc gggctttgcc cggcggcct cagtgagcga gcgagcgcgc cagctggcgt    960
aatagcgaag aggcccgcac cgatcgccct cccaacagt tgcgcagcct gaatggcgaa   1020
tggaattcca gacgattgag cgtcaaaatg taggtatttc catgagcgtt tttcctgttg  1080
caatggctgg cggtaatatt gttctggata ttaccagcaa ggccgatagt ttgagttctt  1140
ctactcaggc aagtgatgtt attactaatc aaagaagtat tgcgacaacg gttaatttgc  1200
gtgatggaca gactctttta ctcggtggcc tcactgatta taaaaacact tctcaggatt   1260
ctggcgtacc gttcctgtct aaaatccctt taatcgcctg cctgtttagc tcccgctctg  1320
attctaacga ggaaagcacg ttatacgtgc tcgtcaaagc aaccatagta cgcgccctgt   1380
agcggcgcat taagcgcggc gggtgtggtg gttacgcgca gcgtgaccgc tacacttgcc   1440
agcgccctag cgcccgctcc tttcgctttc ttccctttcct ttctcgccac gttcgccggc  1500
tttcccccgtc aagctctaaa tcgggggctc cctttagggt tccgatttag tgctttacgg  1560
cacctcgacc ccaaaaaact tgattagggt gatggttcac gtagtgggcc atcgccctga   1620
tagacggttt tcgccctttt gacgttggag tccacgttct ttaatagtgg actcttgttc   1680
caaactggaa caacactcaa ccctatctcg gtctattctt ttgatttata agggattttg  1740
ccgatttcgg cctattggtt aaaaaatgag ctgatttaac aaaaatttaa cgcgaatttt   1800
aacaaaatat taacgtttac aatttaaata tttgcttata caatcttcct gttttttgggg  1860
cttttctgat tatcaaccgg ggtacatatg attgacatgc tagttttacg attaccgttc   1920
atcgattctc ttgtttgctc cagactctca ggcaatgacc tgatagcctt tgtagagacc   1980
tctcaaaaat agctaccctc tccggcatga atttatcagc taaacggtt gaatatcata   2040
ttgatggtga tttgactgtc tccggccttt ctcaccgtt tgaatcttta cctacacatt   2100
actcaggcat tgcatttaaa atatatgagg gttctaaaaa tttttatcct tgcgttgaaa  2160
taaaggcttc tcccgcaaaa gtattacagg gtcataatgt ttttggtaca accgatttag  2220
ctttatgctc tgaggcttta ttgcttaatt tgcttaattc tttgccttgc ctgtatgatt  2280
tattggatgt tggaattcct gatgcggtat tttctcctta cgcatctgtg cggtatttca  2340
caccgcatat ggtgcactct cagtacaatc tgctctgatg ccgcatagtt aagccagccc  2400
cgacacccgc caacacccgc tgacgcgccc tgacgggctt gtctgctccc ggcatccgct   2460
tacagacaag ctgtgaccgt ctccgggagc tgcatgtgtc agaggttttc accgtcatca  2520
ccgaaacgcg cgagacgaaa gggcctcgtg atacgcctat ttttataggt taatgtcatg   2580
ataataatgg tttcttagac gtcaggtggc acttttcggg gaaatgtgcg cggaacccct   2640
atttgtttat ttttctaaat acattcaaat atgtatccgc tcatgagaca ataaccctga  2700
taaatgcttc aataatattg aaaaaggaag agtatgagta ttcaacattt ccgtgtcgcc  2760
cttattccct ttttttgcggc attttgcctt cctgtttttg ctcacccaga aacgctggtg  2820
aaagtaaaag atgctgaaga tcagttgggt gcacgagtgg gttacatcga actggatctc   2880
aacagcggta agatccttga gagttttcgc cccgaagaac gttttccaat gatgagcact   2940
tttaaagttc tgctatgtgg cgcggtatta tccgtattg acgccgggca agagcaactc   3000
ggtcgccgca tacactattc tcagaatgac ttggttgagt actcaccagt cacagaaaag   3060
catcttacgg atggcatgac agtaagagaa ttatgcagtg ctgccataac catgagtgat   3120
aacactgcgg ccaacttact tctgacaacg atcggaggac cgaaggagct aaccgctttt   3180
ttgcacaaca tgggggatca tgtaactcgc cttgatcgtt gggaaccgga gctgaatgaa   3240
gccataccaa acgacgagcg tgacaccacg atgcctgtag caatggcaac aacgttgcgc  3300
aaactattaa ctggcgaact acttactcta gcttcccggc aacaattaat agactggatg  3360
gaggcggata aagttgcagg accacttctg cgctcggccc ttccggctgg ctggtttatt  3420
gctgataaat ctggagccgg tgagcgtggg tctcgcggta tcattgcagc actggggcca  3480
gatggtaagc cctcccgtat cgtagttatc tacacgacgg ggagtcaggc aactatggat  3540
gaacgaaata gacagatcgc tgagataggt gcctcactga ttaagcattg gtaactgtca  3600
gaccaagttt actcatatat actttagatt gatttaaaac ttcattttta atttaaaagg  3660
atctaggtga agatcctttt tgataatctc atgaccaaaa tcccttaacg tgagttttcg   3720
ttccactgag cgtcagaccc cgtagaaaag atcaaaggat cttcttgaga tccttttttt   3780
ctgcgcgtaa tctgctgctt gcaaacaaaa aaaccaccgc taccagcggt ggtttgtttg  3840
ccggatcaag agctaccaac tctttttccg aaggtaactg gcttcagcag agcgcagata  3900
ccaaatactg tccttctagt gtagccgtag ttaggccacc acttcaagaa ctctgtagca  3960
ccgcctacat acctcgctct gctaatcctg ttaccagtgg ctgctgccag tggcgataag  4020
tcgtgtctta ccgggttgga ctcaagacga tagttaccgg ataaggcgca gcggtcgggc  4080
tgaacggggg gttcgtgcac acagcccagc ttggagcgaa cgacctacac cgaactgaga  4140
tacctacagc gtgagctatg agaaagcgcc acgcttcccg aagggagaaa ggcggacagg  4200
tatccggtaa gcggcagggt cggaacagga gagcgcacga gggagcttcc agggggaaac  4260
gcctggtatc tttatagtcc tgtcgggttt cgccacctct gacttgagcg tcgatttttg  4320
tgatgctcgt caggggggcg gagcctatg aaaaacgcca gcaacgcggc cttttacgg    4380
ttcctggcct tttgctggcc ttttgctcac atgttctttc ctgcgttatc ccctgattct  4440
gtggataacc gtattaccgc ctttgagtga gctgataccg ctcgccgcag ccgaacgacc  4500
gagcgcagcg agtcagtgag cgaggaagcg gaagagcgcc caatacgcaa accgcctctc  4560
cccgcgcgtt ggccgattca ttaatgcagc agctgcgcgc tcgctcgctc actgaggccg  4620
cccgggcaaa gcccgggcgt cgggcgacct tggtcgccc ggcctcagtg agcgagcgag   4680
cgcgcagaga gggagtggcc aactccatca ctaggggttc cttgtagtta atgattaacc  4740
cgccatgcta cttatctacg tagccatgct ctaggacatt gattattgac tagtggagtt  4800
ccgcgttaca taacttacgg taaatggccc gcctggctga ccgcccaacg accccgccc   4860
attgacgtca ataatgacgt atgttcccat agtaacgcca atagggactt tccattggtt  4920
tcaatgggtg gagtatttac ggtaaactgc ccacttggca gtacatcaag tgtatcatat  4980
gccaagtacg ccccctattg acgtcaatga cggtaaatgg cccgcctggc attatgccca  5040
gtacatgacc ttatgggact ttcctacttg gcagtacatc tacgtattag tcatcgctat  5100
taccatggtc gaggtgagcc ccacgttctg cttcactctc cccatctccc cccctcccc    5160
accccaatt ttgtatttat ttattttta attatttgt gcagcgatgg gggcggggggg   5220
```

-continued

```
ggggggggc gcgcgccagg cggggcgggg cggggcgagg ggcgggcgg ggcgaggcgg    5280
agaggtgcgg cggcagccaa tcagagcggc gcgctccgaa agtttcctt tatggcgagg    5340
cggcggcggc ggcggcccta taaaaagcga agcgcgcggc gggcgggagt cgctgcgcgc   5400
tgccttcgcc ccgtgccccg ctccgccgcc gcctcgcgcc gcccgccccg gctctgactg   5460
accgcgttac taaaacaggt aagtccggcc tccgcgccgg gttttggcgc ctcccgcggg   5520
cgccccctc ctcacggcga gcgctgccac gtcagacgaa gggcgcagcg agcgtcctga    5580
tccttccgcc cggacgctca ggacagcggc ccgctgctca taagactcgg ccttagaacc   5640
ccagtatcag cagaaggaca ttttaggacg ggacttgggt gactctaggg cactggtttt   5700
ctttccagag agcggaacag gcgaggaaaa gtagtccctt ctcggcgatt ctgcggaggg   5760
atctccgtgg ggcggtgaac gccgatgatg cctctactaa ccatgttcat gttttctttt   5820
tttttctaca ggtcctgggt gacgaacagg gtaccgccac catggcgacg ggttcaagaa   5880
cttccctact tcttgcattt ggcctgcttt gtttgccgtg gttacaggag ggctcggcaa   5940
tgagcgatca ggaagcgaaa ccgagcaccg aagatctggg cgataaaaaa gaaggcgaat   6000
atattaaact gaaagtgatt ggccaggata gcagcgaaat tcattttaaa gtgaaaatga   6060
ccacccatct gaaaaaactg aaagaaagct attgccagcg ccagggcgtg ccgatgaaca   6120
gcctgcgctt tctgtttgaa ggccagcgca ttgcggataa ccataccccg aaagaactgg   6180
gcatggaaga agaagatgtg attgaagtgt atcaggaaca gaccggcggc catagcaccg   6240
tgtctagaga t                                                       6251
```